US00PP34799P2

(12) United States Plant Patent
van Dijk

(10) Patent No.: US PP34,799 P2
(45) Date of Patent: Dec. 6, 2022

(54) ***HYDRANGEA* PLANT NAMED 'HIVAL'**

(50) Latin Name: *Hydrangea macrophylla*
Varietal Denomination: HIVAL

(71) Applicant: Roy Robin van Dijk, De Lier (NL)

(72) Inventor: Roy Robin van Dijk, De Lier (NL)

(73) Assignee: HI BREEDING B.V., DeLier (NL)

( * ) Notice: Subject to any disclaimer, the term of this patent is extended or adjusted under 35 U.S.C. 154(b) by 53 days.

(21) Appl. No.: 17/688,860

(22) Filed: Mar. 7, 2022

(51) Int. Cl.
*A01H 6/48* (2018.01)
*A01H 5/02* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — C. Anne Whealy

(57) ABSTRACT

A new and distinct cultivar of *Hydrangea* plant named 'HIVAL', characterized by its upright and broadly spreading plant habit; moderately vigorous and moderate growth rate; freely branching habit; strong and sturdy stems; dark green-colored leaves; freely flowering habit; large and dense inflorescences with white-colored sterile flowers; and good post-production longevity.

2 Drawing Sheets

Figure 1:
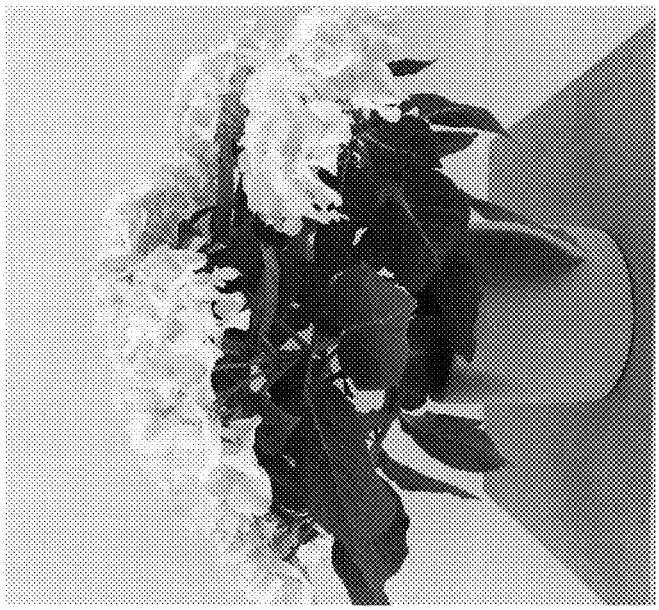

Botanical designation: *Hydrangea macrophylla.*
Cultivar denomination: 'HIVAL'.

STATEMENT REGARDING PRIOR DISCLOSURES BY INVENTOR/APPLICANT & ASSIGNEE

An European Community Plant Breeder's Rights application for the instant plant was filed by the Applicant/Assignee of the instant application, Hi Breeding B.V. of De Lier, The Netherlands on Nov. 15, 2021, application number 2021/2943. Foreign priority is not claimed to this European Plant Breeder's Rights application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HIVAL'.

The new *Hydrangea* plant is a product of a planned breeding program conducted by the Inventor in De Lier, The Netherlands. The objective of the breeding program is to create new sturdy and strong *Hydrangea* plants with attractive inflorescences and good postproduction longevity.

The new *Hydrangea* plant originated from a cross-pollination on Apr. 5, 2016 of a proprietary selection of *Hydrangea macrophylla* identified as code number 1340, not patented, as the female, or seed, parent with a proprietary selection of *Hydrangea macrophylla* identified as code number 1693, not patented, as the male, or pollen, parent. The new *Hydrangea* plant was discovered and selected as a single flowering plant from within the progeny of the stated cross-pollination in a controlled greenhouse environment in De Lier, The Netherlands on Jun. 12, 2018.

Asexual reproduction of the new *Hydrangea* plant by terminal vegetative cuttings since Jul. 12, 2018 in a controlled greenhouse environment in De Lier, The Netherlands has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HIVAL'. These characteristics in combination distinguish 'HIVAL' as a new and distinct *Hydrangea* plant:

1. Upright and broadly spreading plant habit.
2. Moderately vigorous and moderate growth rate.
3. Freely branching habit.
4. Strong and sturdy stems.
5. Dark green-colored leaves.
6. Freely flowering habit.
7. Large and dense inflorescences with white-colored sterile flowers.
8. Good post-production longevity.

Plants of the new *Hydrangea* can be compared to plants of the female parent selection. Plants of the new *Hydrangea* differ primarily from plants of the female parent selection in the following characteristics:

1. Plants of the new *Hydrangea* are not as vigorous as plants of the female parent selection.
2. Stems of plants of the new *Hydrangea* are sturdier than stems of plants of the female parent selection.

Plants of the new *Hydrangea* can be compared to plants of the male parent selection. Plants of the new *Hydrangea* differ primarily from plants of the male parent selection in branching habit as plants of the new *Hydrangea* are more freely branching than plants of the male parent selection.

Plants of the new *Hydrangea* can be compared to plants of *Hydrangea macrophylla* 'Schneeball', not patented. In side-by-side comparisons, plants of the new *Hydrangea* differ primarily from plants of 'Schneeball' in stem strength as stems of plants of the new *Hydrangea* are sturdier than stems of plants of 'Schneeball'.

Plants of the new *Hydrangea* can also be compared to plants of *Hydrangea macrophylla* 'Horklewi', not patented. In side-by-side comparisons, plants of the new *Hydrangea* differ primarily from plants of 'Horklewi' in stem strength as stems of plants of the new *Hydrangea* are sturdier than stems of plants of 'Horklewi'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HIVAL' grown in a container.

Figure 2:
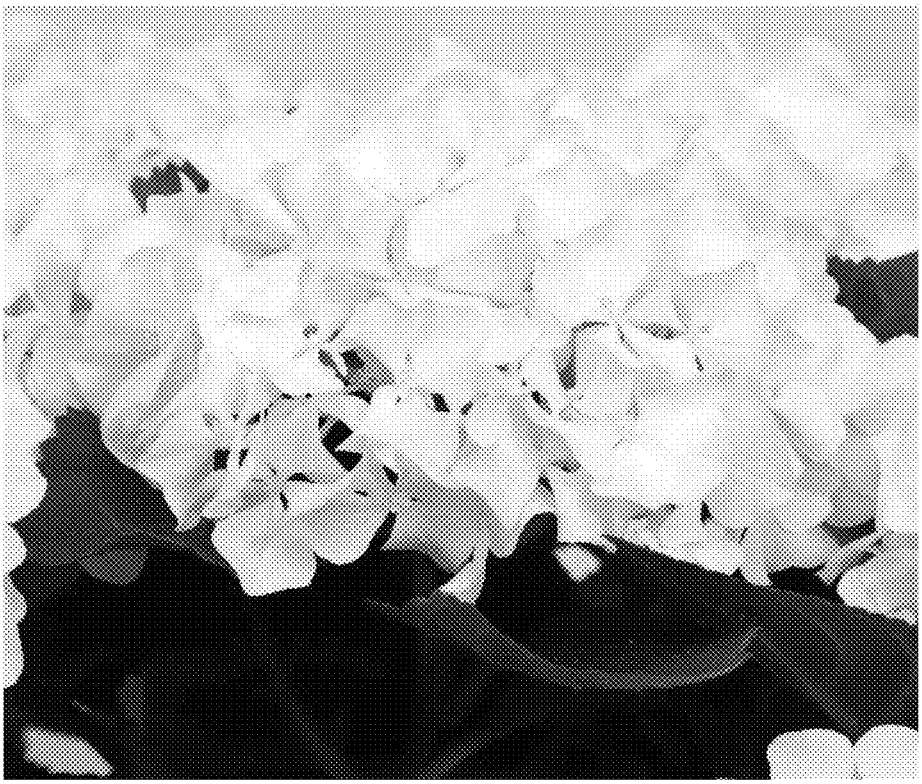

The photograph at the top of the second sheet (FIG. 2) is a close-up view of typical inflorescences of 'HIVAL'.

Figure 3:
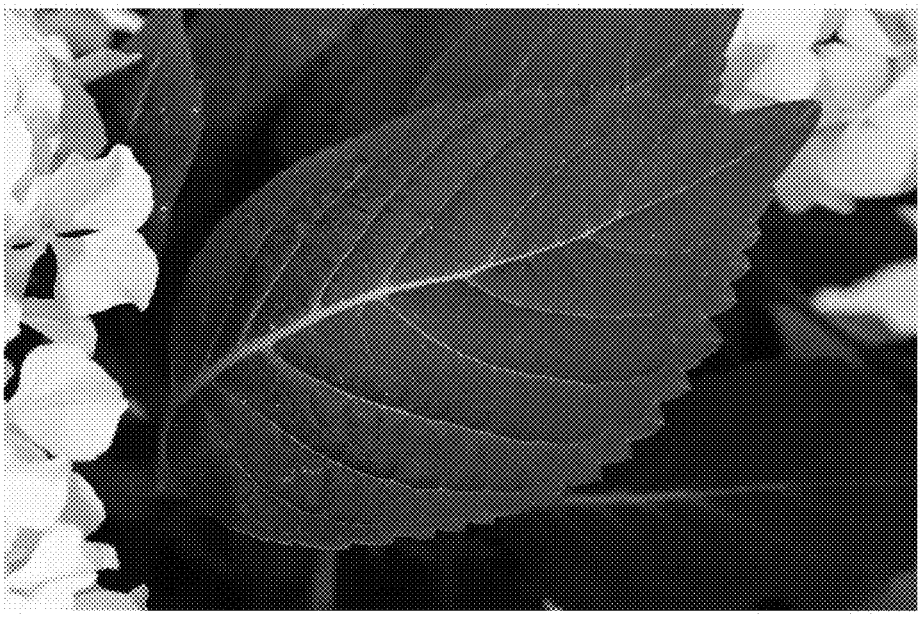

The photograph at the bottom of the second sheet (FIG. 3) is a close-up view of a typical leaf of 'HIVAL'.

DETAILED BOTANICAL DESCRIPTION

Plants used in the aforementioned photographs and in the following description were grown during the spring in 14-cm containers in a glass-covered greenhouse in De Lier, The Netherlands and under cultural practices typical of commercial *Hydrangea* production. During the production of the plants, day temperatures ranged from 20° C. to 35° C., night temperatures ranged from 10° C. to 22° C. and light levels averaged 4,000 lux. Plants of the new *Hydrangea* were pinched one time and were 18 months old when the photographs and description were taken. In the following description, color references are made to The Royal Horticultural Society Colour Chart, 2015 Edition, except where general terms of ordinary dictionary significance are used. As with white-colored flowers, plants of the new *Hydrangea* are not treated with aluminum sulfate to "blue" the flower color.

Botanical description: *Hydrangea macrophylla* 'HIVAL'.

Parentage:

*Female, or seed, patent.*—Proprietary selection of *Hydrangea macrophylla* identified as code number 1340, not patented.

*Male, or pollen, patent.*—Proprietary selection of *Hydrangea macrophylla* identified as code number 1693, not patented.

Propagation:

*Type cutting.*—By vegetative terminal cuttings.

*Time to initiate roots, summer.*—About twelve days at temperatures about 22° C.

*Time to initiate roots, winter.*—About two weeks at temperatures about 20° C.

*Time to produce a rooted young plant, summer.*—About four weeks at temperatures about 22° C.

*Time to produce a rooted young plant, winter.*—About one month at temperatures about 19° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Upright, broadly outwardly spreading and mounding plant habit; flattened globular in overall shape; strong and sturdy stems; moderately vigorous growth habit and moderate growth rate; about six months from propagation are required to produce small finished flowering plants.

*Plant height.*—About 34.7 cm.

*Plant diameter or area of spread.*—About 55.4 cm.

Lateral branch description:

*Branching habit.*—Freely branching habit with about 16 lateral branches per plant; pinching enhances lateral branch development.

*Length.*—About 15.4 cm.

*Diameter.*—About 7 mm

*Internode length.*—About 4.1 cm.

*Strength.*—Strong, sturdy.

*Aspect.*—About 35° from vertical.

*Texture, developing.*—Smooth, glabrous.

*Texture, developed.*—Smooth, glabrous; becoming woody with subsequent development.

*Color, developing.*—Close to 146A and at the nodes, slightly tinged with close to 182A.

*Color, fully developed.*—Close to 144A and at the nodes, slightly tinged with close to 178B; when woody, close to 199A and N199B.

*Lenticels.*—Density: Medium density. Length: About 1 mm. Diameter: About 0.5 mm. Color: Close to a blend of 183A and 200B.

Leaf description:

*Arrangement.*—Opposite, simple.

*Length.*—About 13.2 cm.

*Width.*—About 9.1 cm.

*Shape.*—Broadly ovate to broadly elliptic.

*Apex.*—Apiculate.

*Base.*—Short attenuate.

*Margin.*—Coarsely crenate-serrate.

*Texture, upper surface.*—Slightly rugose, glabrous.

*Texture, lower surface.*—Moderately rugose; small tufts of pubescence at vein axils.

*Venation pattern.*—Pinnate.

*Color.*—Developing leaves, upper surface: Close to NN137A. Developing leaves, lower surface: Close to 138A. Fully developed leaves, upper surface: Darker than a blend of 147A and N189A; venation, close to 144A. Fully developed leaves, lower surface: Close to NN137D; venation, close to 146C.

*Petioles.*—Length: About 2.8 cm. Diameter: About 4 mm to 4.5 mm. Texture and luster, upper and lower surfaces: Smooth, glabrous; slightly glossy. Color, upper surface: Close to 148A; towards the margins, close to 144A. Color, lower surface: Close to 146C.

Flower description:

*Flower type and habit*.—Showy rotate sterile flowers and small, inconspicuous rotate fertile flowers arranged on mophead-type terminal panicles; panicles flattened globular in shape; sterile flowers face upright to outwardly and fertile flowers mostly upright.

*Fragrance*.—None detected.

*Natural flowering season*.—In the garden, plants flower continuously from the late spring to late summer in The Netherlands; flower dormancy can be broken with a cold storage treatment.

*Flower longevity*.—Good postproduction longevity; sterile flowers maintain good substance for about six weeks on the plant, sterile flowers persistent; fertile flowers last for a few days on the plant, fertile flowers not persistent.

*Quantity of flowers*.—Freely flowering habit; about 180 sterile flowers per panicle and about 55 fertile flowers per panicle.

*Panicle height*.—About 10.9 cm.

*Panicle diameter*.—About 17.3 cm.

*Panicle peduncles*.—Length: About 5.5 cm. Diameter: About 3.5 mm. Strength: Strong. Aspect: Primary peduncles, mostly erect; lateral peduncles, about 35° from primary peduncle axis. Texture: Moderately pubescent. Color: Close to 144B; at the nodes, slightly tinged with close to 176B to lighter than 176B.

*Sterile flower buds*.—Length: About 6 mm. Diameter: About 1.6 cm. Shape: Irregular and broadly cup-shaped. Color: Close to 145C.

*Fertile flower buds*.—Length: About 4 mm. Diameter: About 3 mm. Shape: Obovate. Color: Close to NN155B and 157A.

*Sterile flower diameter*.—About 3.1 cm to 5.4 cm.

*Sterile flower depth* (*height*).—About 1.2 cm to 2.2 cm.

*Fertile flower diameter*.—About 7 mm.

*Fertile flower depth* (*height*).—About 6 mm.

*Petals, sterile flowers*.—Quantity and arrangement: Four in a single whorl. Length: About 2.5 mm. Width: About 1.5 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155D; color does not change with subsequent development. When opening and fully opened, lower surface: Close to NN155D; color does not change with subsequent development.

*Petals, fertile flowers*.—Quantity and arrangement: Five in a single whorl. Length: About 3 mm. Width: About 1.75 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155B; color does not change with subsequent development. When opening and fully opened, lower surface: Close to NN155A; color does not change with subsequent development.

*Sepals, sterile flowers*.—Quantity and arrangement: Typically four, or occasionally five, in a single whorl; slightly to moderately imbricate. Length: About 1.8 cm to 2.5 cm. Width: About 1.8 cm to 3 cm. Shape: Broadly rhomboidal to narrowly reniform. Apex: Obtuse to rounded. Base: Cuneate to truncate. Margin: Entire; coarsely undulate. Texture and luster, upper and lower surfaces: Smooth, glabrous; matte. Color: When opening, upper and lower surfaces: Close to NN155D. Fully opened, upper and lower surfaces: Close to NN155D and towards the apex, close to NN155B; with subsequent development, color becoming closer to NN155B.

*Sepals, fertile flowers*.—Quantity and arrangement: Five in a single whorl. Length: About 2 mm. Width: About 1 mm. Shape: Ovate. Apex: Acute. Base: Cuneate. Margin: Entire. Texture and luster, upper and lower surfaces: Smooth, glabrous; matte. Color: When opening and fully opened, upper surface: Close to 157D to lighter than 157D; color does not change with subsequent development. When opening and fully opened, lower surface: Close to 157D to lighter than 157D; color does not change with subsequent development.

*Pedicels, sterile flowers*.—Length: About 1.9 cm. Diameter: About 1.5 mm. Strength: Moderately strong. Aspect: About 30° from main peduncle axis Texture and luster: Densely pubescent; matte. Color: Close to 155C.

*Pedicels, fertile flowers*.—Length: About 0.5 mm. Diameter: About 0.1 mm. Strength: Moderately strong. Aspect: About 10° from vertical. Texture and luster: Densely pubescent; matte. Color: Close to 157C and 157D.

*Reproductive organs, sterile flowers*.—Stamens: Quantity per flower: Eight. Filament length: About 2 mm. Filament color: Close to NN155D. Anther shape: Broadly oblong. Anther length: About 0.5 mm. Anther color: Close to 155D. Pollen amount: Moderate. Pollen color: Close to 155D. Pistils: Pistil quantity per flower: Three. Pistil length: About 1 mm. Stigma shape: Club-shaped. Stigma color: Close to 155A. Style length: About 0.5 mm. Style color: Close to NN155A. Ovary color: Close to 157D.

*Reproductive organs, fertile flowers*.—Stamens: Quantity per flower: Ten. Filament length: About 3.5 mm. Filament color: Close to N155B. Anther shape: Broadly oblong. Anther length: About 1 mm. Anther color: Close to 155D. Pollen amount: Moderate. Pollen color: Close to 155D. Pistils: Pistil quantity per flower: Three. Pistil length: About 2 mm. Stigma shape: Club-shaped. Stigma color: Close to 157D to lighter than 157D. Style length: About 1 mm. Style color: Close to 157C to 157D. Ovary color: Close to 157C.

*Seeds*.—To date, seed development has not been observed on plants of the new *Hydrangea*.

Pathogen & pest resistance: Plants of the new *Hydrangea* have been observed to be tolerant to *Botrytis* (*Botrytis cinerea*). To date, plants of the new *Hydrangea* have not been observed to be resistant to pests and other pathogens common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HIVAL' as illustrated and described.

* * * * *